United States Patent [19]

Pretzer et al.

[11] 4,239,925

[45] Dec. 16, 1980

[54] ETHANOL FROM METHANOL

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[21] Appl. No.: 42,516

[22] Filed: May 25, 1979

Related U.S. Application Data

[63] Continuation-in-part of Ser. No. 863,743, Dec. 23, 1977, abandoned.

[51] Int. Cl.$^3$ .............................................. C07C 27/00
[52] U.S. Cl. ................................. 568/902; 560/265; 568/671; 568/487
[58] Field of Search ........................................ 568/902

[56] References Cited

U.S. PATENT DOCUMENTS

| | | | |
|---|---|---|---|
| 3,248,432 | 4/1966 | Riley et al. | 568/902 |
| 3,418,351 | 12/1968 | Greene et al. | 568/909 |
| 3,448,157 | 6/1969 | Slaugh et al. | 568/909 |

OTHER PUBLICATIONS

Wender et al, "Science", vol. 113 (1951), pp. 206–207.

*Primary Examiner*—Joseph E. Evans

[57] ABSTRACT

A process for selectively producing ethanol which comprises introducing into a reaction zone methanol, hydrogen, carbon monoxide, a cobalt tricarbonyl complex and an iodine promoter and then subjecting the contents of said reaction zone to an elevated temperature and an elevated pressure for a time period sufficient to convert methanol to ethanol.

17 Claims, No Drawings

ETHANOL FROM METHANOL

This is a continuation-in-part application of our application Ser. No. 863,743 entitled A PROCESS FOR HOMOLOGATION OF METHANOL TO ETHANOL WITH HIGH SELECTIVITY USING A COBALT TRICARBONYL COMPLEX AND AN IODINE PROMOTER filed Dec. 23, 1977, and now abandoned.

BACKGROUND OF THE INVENTION

1. Field of the Invention

Ethanol is a compound which has been used by man since time immemorial. Historically, ethanol has been produced for various purposes by the fermentation of common grains. However, within recent years synthetic processes have been developed to synthesize this alcohol for industrial use. Such synthetic processes permit the use of more economical starting materials than those used in the fermentation processes, and, additionally, permit production and reproduction of a more standardized product and more easily predictable yields of end product. Methanol can easily and economically be produced in great quantities from hydrogen and carbon monoxide or from almost anything containing carbon and hydrogen, for example, from methane to manure and from coal to crude oil residues. One such process for producing ethanol synthetically involves reacting methanol with carbon monoxide and hydrogen at elevated temperatures and pressures in the presence of a catalyst system.

The conversion of an alcohol, for example, methanol, to the primary alcohol containing one carbon atom more than the original alcohol, namely ethanol, is normally a tedious and time-consuming procedure involving a series of steps. Additionally, catalysts which possess acceptable activity generally tend to give a wide spectrum of products in addition to ethanol, for example, hydrocarbons and oxygenated hydrocarbons having a broad distribution of carbon atoms. This not only complicates the separation and recovery of desired products, but results in reduced yield of ethanol and erosion of reactants in the production of undesirable by-products.

2. Description of the Prior Art

The reaction of methanol with hydrogen and carbon monoxide to produce ethanol is appreciated and disclosed by the prior art. However, in general, most known processes produce an undesirably large mixture of alcohols, aldehydes, ketones and carboxylic acids in addition to the desired alcohol. For example, U.S. Pat. No. 4,013,700, entitled "Catalytic Process for Polyhydric Alcohols and Derivatives", issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled "Process for the Production of Ethyl Alcohol", issued to Riley et al, on Apr. 26, 1966, which relates to a process for the production of ethyl alcohol by the interaction of methanol, carbon monoxide and hydrogen. In particular, these compounds are reacted at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled "Preparation of Organic Hydroxy-Containing Compounds by Reacting Alcohols With Carbon Monoxide and Hydrogen", issued to Gresham on Dec. 30, 1952, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt hydride, metallic cobalt, and organic and inorganic cobalt salts. The process, however, suffers from the disadvantage or poor product distribution.

U.S. Pat. No. 3,285,948, entitled "Halides of Ruthenium and Osmium In Conjunction With Cobalt and Iodine in the Production of Ethanol from Methanol", issued to Butter on Nov. 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, iodine or alkali metal iodines. A secondary promoter is also employed, i.e., ruthenium halide or osmium halide. High selectivity is described as better when the secondary promoter is used in combination with the primary promoter and other reactants.

Dutch Pat. No. 7606138, entitled "Process for the Formation of Ethanol from Methanol and Synthesis Gas", issued to Shell International Research on June 8, 1976, relates to a process for producing alcohols which utilizes any soluble cobalt source which can generate a cobalt carbonyl or hydro carbonyl by reaction with synthesis gas. For example, sources of cobalt suitable for use are cobalt iodide or cobalt metal from which ions can be generated in-situ. Organic salts of cobalt such as cobalt acetate, formate or propionate are described as especially good sources; an iodide or bromide promoter is also utilized. In addition, the use of a tertiary phosphine is described as affording improved selectivity to the formation of alcohols.

Unexpectedly, we have discovered that not all cobalt sources give similar results, that is, produce a product containing a large amount of ethanol with a minimum amount of other products. Generally, catalysts which possess excellent activity tend to give a wide spectrum of products, for example, hydrocarbons and oxygenated hydrocarbons having a product distribution of varying carbon atom content. This not only complicates the recovery of desired products, but results in the wastage of reactants to commercially uninteresting by-products.

SUMMARY OF THE INVENTION

The present invention relates to a process for the selective homologation of methanol to ethanol which comprises introducing into a reaction zone methanol, hydrogen, carbon monoxide, a cobalt tricarbonyl complex and an iodine promoter and then subjecting the contents of said reaction zone to an elevated temperature and an elevated pressure for a time period sufficient to convert methanol to ethanol.

Although hydrogen and carbon monoxide are employed herein for reaction with methanol to produce ethanol, it is understood that any combination of compounds that will form hydrogen and carbon monoxide in the reaction zone can also be used, for example, mixtures of hydrogen and carbon dioxide, water and carbon monoxide, etc. The mixture of hydrogen and carbon monoxide used herein can be produced from anything containing carbon and hydrogen. Two types of reactions, for example, can be used for the production of synthesis gas: partial oxidation and steam reforming. Steam reforming is the more important process when natural gas (methane) is the hydrogen-carbon source. Partial oxidation is used primarily for heavy fuel and residue. The relative amounts of hydrogen and carbon monoxide present in the reaction mixture can be varied over a wide range. However, in general, the molar ratio of hydrogen to carbon monoxide is from about 10:1 to about 1:10, especially from about 3:1 to about 1:3; however, conventional synthesis gas (mixtures of hydrogen to carbon monoxide) with a ratio of about 1:1 is convenient and satisfactory for the process herein. It is to be noted that molar ratios outside the aforestated ratio ranges can be employed, and, as pointed out hereinabove, compounds or reaction mixtures which give rise to the formation of carbon monoxide and hydrogen under the reaction conditions defined herein can be used instead of mixtures comprising hydrogen and carbon monoxide which are used in the preferred embodiments of this invention.

The cobalt tricarbonyl complex used herein can be defined by the formula:

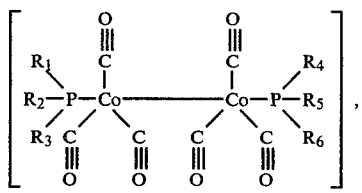

wherein $R_1$, $R_2$, $R_3$, $R_4$, $R_5$ and $R_6$, the same or different, are selected from the group consisting of saturated or unsaturated, straight or branched chain, alkyl radicals having from one to 24 carbon atoms, preferably from two to 10 carbon atoms, aryl radicals having from six to 20 carbon atoms, preferably from six to 10 carbon atoms, alkenyl radicals having from two to 30 carbon atoms, preferably from two to 20 carbon atoms, cycloalkyl radicals having from three to 40 carbon atoms, preferably from three to 30 carbon atoms, and aralkyl and alkaryl radicals having from six to 40 carbon atoms, preferably from six to about 30 carbon atoms.

Cobalt tricarbonyl complexes which are suitable for use herein include:
triethyl phosphine cobalt tricarbonyl dimer
tri-n-butyl phosphine cobalt tricarbonyl dimer
tri-isopropyl phosphine cobalt tricarbonyl dimer
tricyclohexyl phosphine cobalt tricarbonyl dimer
tricycloheptyl phosphine cobalt tricarbonyl dimer
diphenyl-methyl phosphine cobalt tricarbonyl dimer
triphenyl phosphine cobalt tricarbonyl dimer
trinaphtha phosphine cobalt tricarbonyl dimer
tristryl phosphine cobalt tricarbonyl dimer
vinyl-diphenyl phosphine cobalt tricarbonyl dimer
tribenzyl phosphine cobalt tricarbonyl dimer, and
tri-para-tolyl phosphine cobalt tricarbonyl dimer, or mixtures thereof.

Any source of iodine which is capable of disassociating, that is, ionizing to form free iodide ions, in the reaction medium can be used as a promoter in the present invention.

Illustrative examples of iodine promoters especially suitable for use herein include iodine, potassium iodide, calcium iodide, sodium iodide, lithium iodide, hydrogen iodide, methyl iodide, ethyl iodide, etc.

The reactant components and catalyst can be used over a relatively wide range. Thus, the molar ratio of cobalt tricarbonyl complex to methanol can be from about 1:1 to about 1:100,000, preferably from about 1:1 to about 1:2000. The iodine promoter and the cobalt tricarbonyl complex can be present in a molar ratio ranging from about 100:1 to about 1:100, preferably from about 10:1 to about 1:10.

Pressures which are suitable for use in the present process generally are above about 1000 psig (6.83 MPA), but should not be in excess of about 10,000 psig (68.30 MPA). An especially desirable pressure range is from about 1000 psig (6.83 MPA) to about 6000 psig (40.98 MPA), preferably from about 2000 psig (13.66 MPA) to about 5000 psig (34.15 MPA). Temperatures which are suitable are those temperatures which initiate a reaction between the reactants herein to produce ethanol, generally from about 150° C. to about 250° C., preferably from about 175° C. to about 225° C. The reaction is conducted for a time period sufficient to convert methanol to ethanol, normally from about 0.5 hour to about 10 hours, especially from about 1 hour to about 5 hours. Recovery of the desired ethanol from the reaction product can be effected in any convenient or conventional manner, for example, by distillation. It should be noted that at ambient pressure and above about 21° C., the components will distill off in the following sequence for the desired recovery: dimethyl ether, diethyl ether, methyl acetate, methanol and ethanol.

In a preferred embodiment, the methanol, hydrogen and carbon monoxide are introduced into a pressure-resistant reaction vessel, for example, a stainless steel autoclave with agitation means. Agitation is defined herein as shaking, rocking, stirring, percolation with synthesis gas, etc. Methanol can conveniently be converted into ethanol in a batch operation or in a continuous process. When the batch method is used, methanol, hydrogen, carbon monoxide, cobalt tricarbonyl complex and iodine promoter are introduced into the reaction vessel and the pressure and temperature are adjusted to the operating reaction conditions. If the system is a closed system, the pressure is raised to the desired level with hydrogen and carbon monoxide before the reaction is initiated and the pressure falls as the reaction proceeds, but never below reaction pressure. Alternatively, the system can be equipped with a reservoir which contains synthesis gas and which feeds said gas to the reaction vessel at a set pressure on demand, thus maintaining a particular pressure level.

In a continuous process for producing ethanol, methanol, synthesis gas, cobalt tricarbonyl complex and iodine promoter are continuously fed into a pressure-resistant reaction vessel as described herein at a constant rate. The cobalt tricarbonyl complex and iodine promoter are normally dissolved in an inert solvent, for example, ethylene glycol, 1,2-dimethoxy ethane, or octane, before introduction into the reaction vessel for ease of application and recovery of the cobalt complex and iodine promoter. The mixture of methanol, synthesis gas, cobalt tricarbonyl complex, and iodine promoter is then reacted under reaction conditions for a time period sufficient to convert methanol to ethanol.

In order to obtain increased yields of ethanol herein it is critical that the cobalt tricarbonyl complex defined above be introduced into the reactor as such rather than introducing a cobalt compound and a phosphine separately therein that might be converted in situ to the desired cobalt complex.

DESCRIPTION OF PREFERRED EMBODIMENTS

A number of runs was carried out as follows.

Into a 300 cc. stainless steel autoclave were charged selected amounts of catalyst, 0.75 millimole of iodine and 100 milliliters of methanol. In each of Examples I and II three millimols of the cobalt tricarbonyl complex were charged. In each of Examples III and IV three millimols of each of the specific phosphines and three millimols of cobalt acetylacetonate were charged. The reactor was next purged twice with nitrogen gas and then pressurized with synthesis gas (hydrogen to carbon dioxide molar ratio=1:1) to a pressure of about 1000 psig (6.83 MPA) lower than the desired working pressure. The system was then heated to a temperature of about 200° C. and the pressure was adjusted to a working pressure of about 4000 psig (27.6 MPA). The reaction was allowed to proceed for approximately three hours, after which the reactor was cooled by an internal cooling coil to about −75° C. The reactor was vented through a dry gas meter, a gas sample was taken for a mass spectral analysis, and the liquid product was analyzed using a Model 900 Perkins-Elmer gas chromatograph utilizing a 16 ft. (4.88 meters)×⅛ in. (0.32 centimeter) stainless steel column wherein 8 ft. (2.44 meters) of the column was packed with 80/100 mesh Poropak Q and the other 8 ft. (2.44 meters) was packed with 80/100 Poropak R. Poropak Q and Poropak R are a form of polyvinyl benzene marketed commercially by Waters Associates, a corporation located in Milford, Massachusetts. The gas chromatograph was programmed to increase from 40° C. to 190° C. at a rate of 32° C./min. and with a helium flow rate at 30 cc/min.

The results obtained are tabulated in Table I below.

compared with Example IV, it can be seen that by following the dictates herein at least six percent higher yield of ethanol is achieved. By comparing Example I with Example IV an improvement in yield in excess of 13 percent is obtained. But if Example II is compared with Example III, it can be seen that an improvement in ethanol yield of at least 46 percent is achieved. A still higher improvement, 61 percent, is obtained by comparing Example I with Example III.

Obviously, many modifications and variations of the invention, as hereinabove set forth, can be made without departing from the spirit and scope thereof, and therefore only such limitations should be imposed as are indicated in the appended claims.

We claim:

1. A process for the homologation of methanol to ethanol which comprises introducing into a reaction zone methanol, hydrogen, carbon monoxide, a cobalt tricarbonyl complex of the formula:

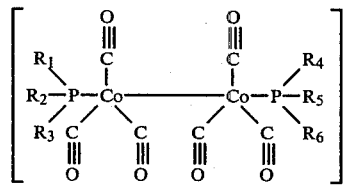

wherein $R_1$, $R_2$, $R_3$, $R_4$, $R_5$ and $R_6$ are aryl radicals having from six to 20 carbon atoms, and an iodine promoter and then subjecting the contents of said reaction zone to an elevated temperature and an elevated pressure for a time period sufficient to convert methanol to ethanol.

2. The process according to claim 1 wherein $R_1$, $R_2$, $R_3$, $R_4$, $R_5$ and $R_6$ are aryl radicals having from six to 10 carbon atoms.

3. The process of claim 1 having a reaction time period of from about 0.5 hour to about 10 hours.

4. The process of claim 1 wherein the cobalt tricarbonyl complex is triphenyl phosphine cobalt tricarbonyl dimer.

TABLE I

| | Catalyst | Percent Methanol Conversion | Selectivity Mol Percent | | | | | Percent Ethanol Yield |
|---|---|---|---|---|---|---|---|---|
| | | | Dimethyl Ether | Ethanol | Acetaldehyde | Methyl Acetate | Other[a] | |
| Ex. I | Tri-n-butyl phosphine cobalt tricarbonyl dimer + iodine | 62.5 | 3.2 | 65.4 | 9.2 | 15.2 | 7.0 | 40.9 |
| Ex. II | Triphenyl phosphine cobalt tricarbonyl dimer + iodine | 63.4 | 4.0 | 60.3 | 13.6 | 13.8 | 8.3 | 38.2 |
| Ex. III | Triphenyl phosphine + cobalt acetylacetonate + iodine | 43.7 | 3.2 | 56.2 | 19.9 | 15.5 | 5.2 | 25.5 |
| Ex. IV | Tri-n-butyl phosphine + cobalt acetylacetonate + iodine | 60.0 | 4.1 | 59.8 | 11.1 | 15.7 | 9.3 | 35.9 |

[a]Mixtures of ethyl acetate, methyl formate, propanols, propionaldehyde, butanols, n-butyraldehyde and methane The results obtained above are most unusual. Note that in each of Examples I and II, carried out in accordance with the procedure defined and claimed herein, the ethanol yield was at least 38.2 percent. When the phosphine and cobalt acetyacetonate were added individually in Examples III and IV the ethanol yield varied from a low of 25.4 percent in Example III to 35.9 percent in Example IV. Thus, even if Example II were 5. The process of claim 1 having a reaction time period of from about 1 hour to about 5 hours.

6. The process according to claim 1 wherein the hydrogen and carbon monoxide are in a molar ratio of from about 10:1 to about 1:10.

7. The process of claim 1 wherein the hydrogen and carbon monoxide are in a molar ratio of from about 3:1 to about 1:3.

8. The process of claim 1 wherein the cobalt tricarbonyl complex and methanol are in a molar ratio of from about 1:1 to about 1:100,000.

9. The process of claim 1 wherein the cobalt tricarbonyl complex and methanol are in a molar ratio of from about 1:1 to about 1:2,000.

10. The process of claim 1 wherein the iodine promoter is a member selected from the group consisting of iodine, potassium iodide, calcium iodide, sodium iodide, lithium iodide, hydrogen iodide, methyl iodide or ethyl iodide.

11. The process of claim 1 wherein the iodine promoter is iodine.

12. The process of claim 1 wherein the cobalt tricarbonyl complex and iodine promoter are in a molar ratio of from about 100:1 to about 1:100.

13. The process of claim 1 wherein the methanol and iodine promoter are in a molar ratio of from about 10:1 to about 1:10.

14. The process according to claim 1 having a reaction temperature of from about 150° C. to about 250° C.

15. The process of claim 1 having a reaction temperature of from about 175° C. to about 225° C.

16. The process of claim 1 having a reaction pressure of from about 1000 psig to about 6000 psig.

17. The process of claim 1 having a reaction pressure of from about 2000 psig to about 5000 psig.

* * * * *